United States Patent [19]
Arnold

[11] Patent Number: 6,050,961
[45] Date of Patent: Apr. 18, 2000

[54] OROMOTOR DYNAMOMETER

[76] Inventor: Robert J. Arnold, 22147 Trace Rd., McCalla, Ala. 35111

[21] Appl. No.: 09/191,585

[22] Filed: Nov. 13, 1998

[51] Int. Cl.[7] .................................................... A61B 5/00
[52] U.S. Cl. .......................................... 600/590; 600/595
[58] Field of Search .................................... 600/587, 590, 600/595; 33/512–514; 73/379.01, 379.02, 379.03, 379.09

[56] References Cited

U.S. PATENT DOCUMENTS

| | | |
|---|---|---|
| 2,708,367 | 5/1955 | Lusk . |
| 3,420,222 | 1/1969 | Noe et al. ................................. 73/658 |
| 4,674,330 | 6/1987 | Ellis ........................................ 73/379 |
| 5,381,799 | 1/1995 | Hamilton et al. ...................... 600/590 |

*Primary Examiner*—Max Hindenburg

[57] ABSTRACT

A system for measuring a plurality of characteristics of a user's oral regions comprising, in combination, a pair of planks each having a proximal end and a distal end. The rods include an upper plank and a lower plank with a hinge coupling the distal ends of the rods. A pair of proximally extending supports each having an exterior surface adapted to be received in the mouth of a user. A deformable pneumatic bulb is positioned between the planks adjacent to the proximal end thereof. A associated tube thereby applies a pneumatic force to the second end of the tube. A meter is coupled to the second end of the tube to provide readings in response to the force applied to the bulb. The tube extends through a hole in the upper plank.

8 Claims, 9 Drawing Sheets

OROMOTOR DYNAMOMETER

BACKGROUND OF THE INVENTION

1. Field of the Invention

The present invention relates to an oromotor dynamometer and more particularly pertains to a system for measuring a plurality of characteristics of a user's oral regions.

2. Description of the Prior Art

The use of medical measurement devices of known designs and configurations is known in the prior art. More specifically, medical measurement devices of known designs and configurations heretofore devised and utilized for the purpose of measuring the oral characteristics through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. Nos. 4,276,445, issued Jun. 30, 1981, and 4,401,850 issued Aug. 30, 1983, to Harleson disclose speech analysis apparatuses. U.S. Pat. No. 5,119,831 issued Jun. 9, 1992, to Robin et al discloses a system and method for detecting pressure of selected body parts. U.S. Pat. No. 5,381,799, issued Jan. 17, 1995, to Hamilton et al discloses a mechanically operated bite force gauge. U.S. Pat. No. 5,452,727, issued Sep. 26, 1995, to Tura, et al discloses an orofacial myographic measurement apparatus. U.S. Pat. No. 5,533,521, issued Jul. 9, 1996, to Granger discloses an interchangeable tissue measuring device. Lastly, U.S. Pat. No. 5,678,317, issued Oct. 21, 1997, to Stefanakos discloses a method for measuring labial/facial flaccidity.

While these devices fulfill their respective, particular objectives and requirements, the aforementioned patents do not describe an oromotor dynamometer that allows measuring varying capacities of a user's oral regions through interchangeable equipment.

In this respect, the oromotor dynamometer according to the present invention substantially departs from the conventional concepts and designs of the prior art, and in doing so provides an apparatus primarily developed for the purpose of measuring varying capacities of a user's oral regions through interchangeable equipment.

Therefore, it can be appreciated that there exists a continuing need for a new and improved oromotor dynamometer which can be used for measuring varying capacities of a user's oral regions through interchangeable equipment. In this regard, the present invention substantially fulfills this need.

SUMMARY OF THE INVENTION

In view of the foregoing disadvantages inherent in the known types of medical measurement devices of known designs and configurations now present in the prior art, the present invention provides an improved oromotor dynamometer. As such, the general purpose of the present invention, which will be described subsequently in greater detail, is to provide a new and improved oromotor dynamometer and method which has all the advantages of the prior art and none of the disadvantages.

To attain this, the present invention essentially comprises a new and improved system for measuring a plurality of characteristics of a user's oral regions. A pair of planks are provided. Each plank has a proximal end and a distal end. The planks include an upper plank and a lower plank. The lower plank is of a length greater than the upper plank. A hinge is provided coupling the distal ends of the planks. An axial recess is formed in the proximal end of each plank with a threaded aperture operatively associated with each recess. A pair of proximally extending supports are provided. The supports have exterior surfaces adapted to be received in the mouth of a user and to be moved toward each other upon the application of the user's teeth toward each other. The supports each have a distal end received within an associated recess adjacent to the proximal end of the upper plank and the proximal end of the lower plank respectively with an associated wing nut for securing the supports to the planks and for allowing the separation therebetween. A deformable pneumatic bulb is positioned between the planks adjacent to the proximal end thereof. An associated tube has a first end coupled to the bulb and adapted to be compressed upon the application of force by a user to the supports through the planks to thereby apply a pneumatic force to the second end of the tube. A meter is coupled to the second end of the tube to provide readings in response to the force applied to the bulb. The tube extends through a hole in the upper plank. An adjustment plate is adjustably secured to the lower surface of the upper plank. A threaded wing nut is adapted to allow the selective positioning of the adjustment plate with respect to the upper plank as a function of the pressure intended to be applied by the user. The adjustment plate includes two parallel guide rods extending upwardly therefrom through parallel apertures in the upper plank. Securement sleeves are provided with apertures and small wing nuts assist in the proper positioning of the adjustment plate.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved oromotor dynamometer which has all of the advantages of the prior art of medical measurement devices of known designs and configurations and none of the disadvantages.

It is another object of the present invention to provide a new and improved oromotor dynamometer which may be easily and efficiently manufactured and marketed.

It is further object of the present invention to provide a new and improved oromotor dynamometer which is of durable and reliable constructions.

An even further object of the present invention is to provide a new and improved oromotor dynamometer which is susceptible of a low cost of manufacture with regard to both materials and labor, and which accordingly is then susceptible of low prices of sale to the consuming public, thereby making such Oromotor dynamometer economically available to the buying public.

Lastly, it is an object of the present invention to provide an oromotor dynamometer for measuring varying capacities of a user's oral regions through interchangeable equipment.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
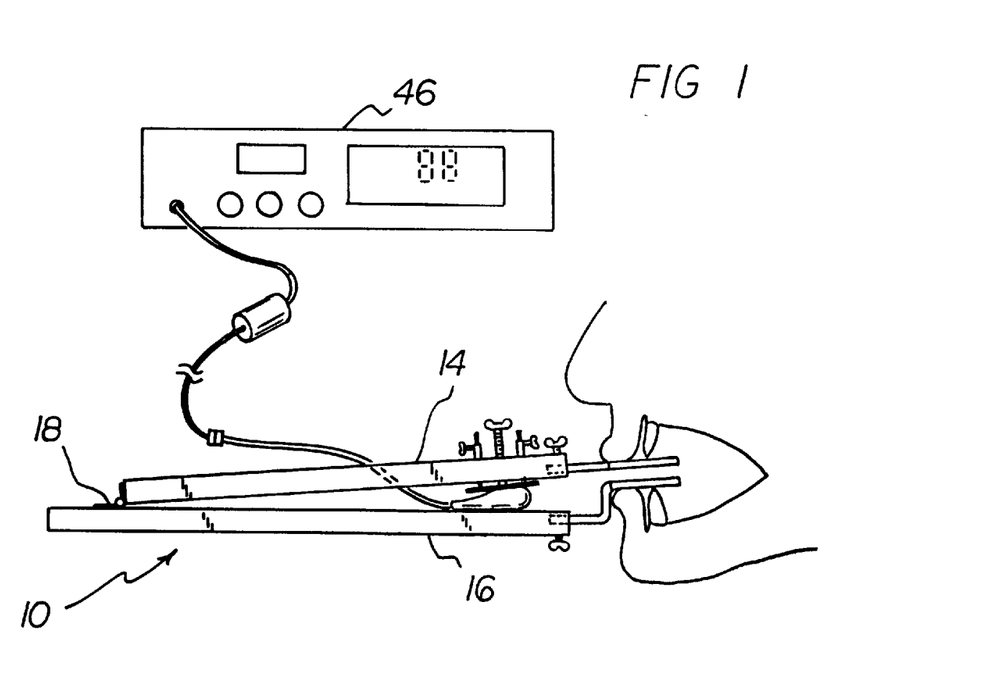
FIG. 1 is a side elevational view of the preferred embodiment of the oromotor dynamometer constructed in accordance with the principles of the present invention.
Figure 2:
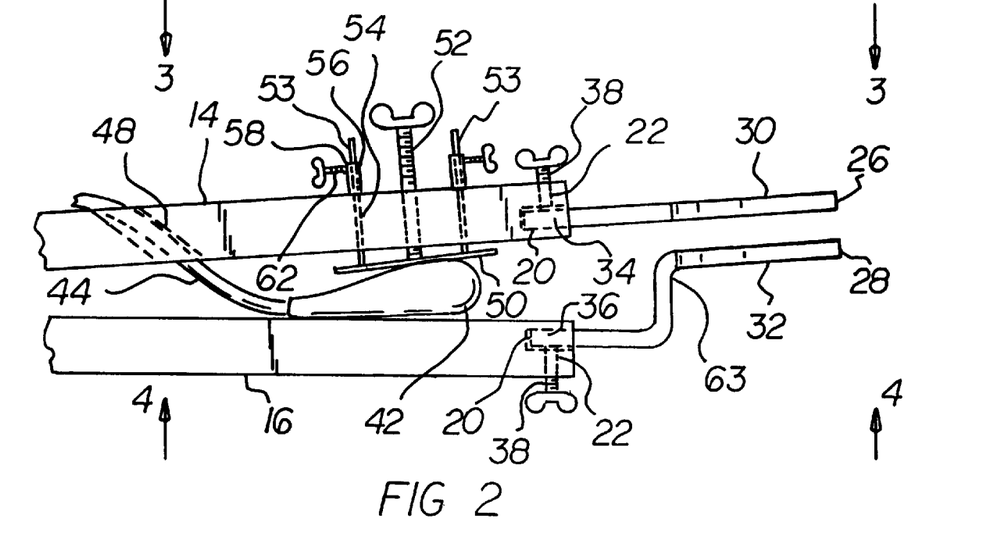
FIG. 2 is an enlarged cross-sectional view of the proximal portion of the device shown in FIG. 1.
Figure 3:
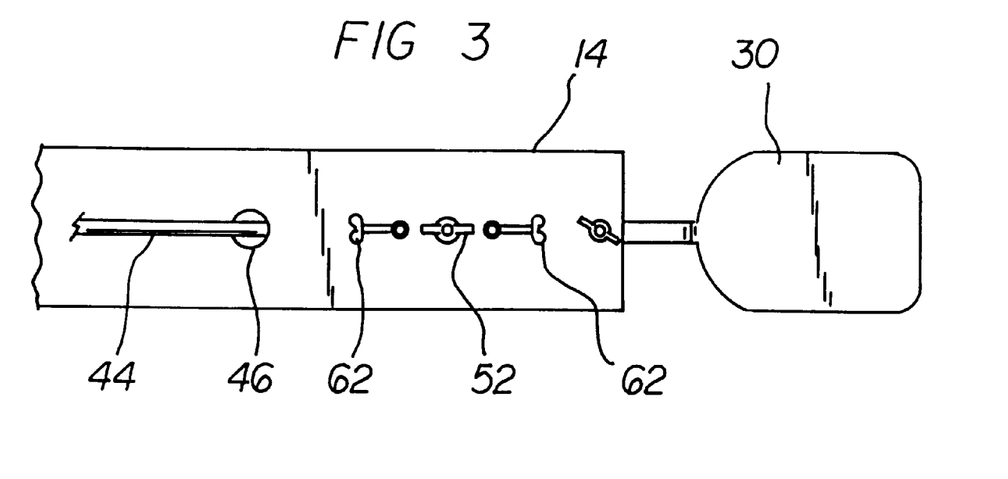
FIG. 3 is a top elevational view taken along line 3—3 of FIG. 2.
Figure 4:
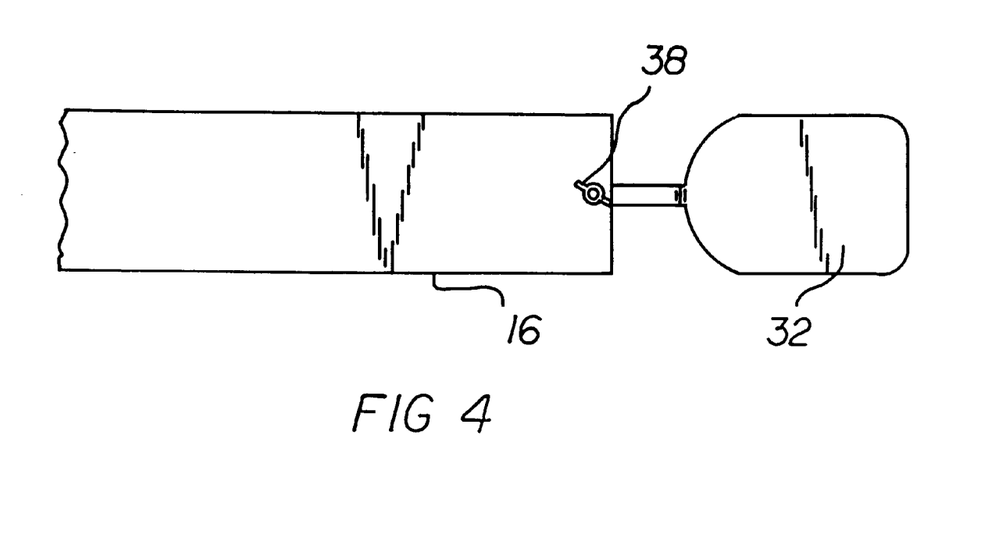
FIG. 4 is a bottom elevational view taken along line 4—4 of FIG. 2.

With reference now to the drawings, and in particular to FIG. 1 thereof, the preferred embodiment of the new and improved oromotor dynamometer embodying the principles and concepts of the present invention and generally designated by the reference numeral 10 will be described.

The present invention, the oromotor dynamometer system 10 is comprised of a plurality of components. Such components in their broadest context include a new and improved system 10 for measuring a plurality of characteristics of a user's oral regions.

Such system comprises, in combination, a pair of planks 14, 16. Each has a proximal end and a distal end. The planks include an upper plank 14 and a lower plank 16. The lower plank is of a length greater than the upper plank. A hinge 18 couples the distal ends of the planks.

An axial recess 20 is formed in the proximal end of each plank. In addition, a threaded aperture 22 is operatively associated with each recess.

A pair of proximally extending supports 26, 28 are next provided. Each support has an exterior surface 30, 32. The exterior surfaces are adapted to be received in the mouth of a user. Such surfaces are adapted to be moved toward each other upon the application of the user's teeth toward each other. The supports each have a distal end 34, 36 received within an associated recess adjacent to the proximal end of the upper plank and the proximal end of the lower plank respectively. An associated wing nut 38 is utilized for securing the supports to the planks and for allowing the separation therebetween for thereby utilizing other supports for different measurements.

A deformable pneumatic bulb 42 is next provided. Such bulb is positioned between the planks adjacent to the proximal end thereof. An associated tube 44 is next provided. Such tube has a first end coupled to the bulb and adapted to be compressed upon the application of force by a user to the supports through the planks. This action functions to apply a pneumatic force which is transferred to the second end of the tube.

A meter 46 is coupled to the second end of the tube. Such meter functions to provide readings of force or duration in response to the force applied to the bulb. The tube extends through a hole 48 in the upper plank.

An adjustment plate 50 is adjustably secured to the lower surface of the upper plank. A threaded wing nut 52 is located in a threaded aperture in the upper plank and is adapted to allow the selective positioning of the adjustment plate with respect to the upper plank. Such subjective positioning functions to vary the pressure intended to be applied by the user. The adjustment plate includes two parallel guide rods 53 extending upwardly therefrom through parallel apertures 54 in the upper plank. Securement sleeves 56 with apertures 58 and small wing nuts 62 assist in the proper positioning of the adjustment plate.

The first embodiment is shown in FIGS. 1–4 and includes a lower support which has a generally z-shaped profile 63 to allow pressure to be applied by a user's teeth. This relates to a mandibular/pincer strain gauge. The mandibular/pincer strain gauge (MPSG) is the basic OD device with the attachment providing upper and lower dental saddles upon which the patient would be required to bite using an incisal bite and/or upon which the patient would be required to pinch with the thumb and index finger of both the left and right hands. This attachment allows the clinician to objectively assess the muscles of the jaw/mandible (e.g. masseters) and to objectively assess the pincer muscles of the left and right hands. Both mandibular strength and mandibular endurance would be assessed as well as pincer strength and pincer endurance of the left and right hands. To assess the mandibular strength and endurance, the MPSG would be placed in between the patient's incisors and the patient would be required to bite the upper and lower dental saddles as hard as he/she comfortably could or until he/she has achieved a "do not exceed" level of bite force". This, in turn, would compress the bulb in the OD. The pressure displacement would be sent through a catheter/plastic tubing from the bulb to a manometer. The manometer would then be read at it's peak pressure to determine the patient's maximum strength with this task. Next, the MPSG would be replaced in the same position between the patient's incisors and the patient would be required to bite the upper and lower dental saddles to the point of resisting 50 percent of his/her maximum strength in KPa and/or mmHg (millimeters of mercury) for an extended duration in seconds. This task would end when the patient was no longer able to resist 50 percent or more of his/her maximum strength in KPa and/or mmHg (millimeters of mercury) or when the patient was no longer able to comfortably perform the task. This task would be the objective measurement of muscle endurance in the parameter of mandibular compression/incisal bite. To better illustrate this, if the patient compressed a maximum of 90 KPa while biting the upper and lower dental saddles during the mandibular strength assessment, then the muscle endurance would be determined objectively be assessing how many seconds the patient could continue to bite with a force greater than or equal to 50 percent of 90 KPa (which would be 45 KPa). The patient could now be required to squeeze the upper and lower dental saddles of the MPSG with his/her thumb and first finger. In this way, the pincer muscle strength and the pincer muscle endurance of both the left and right hands could be assessed by requiring the patient to pinch the dental saddles as hard as he/she could and reading the manometer to assess patient's maximum pincer muscle strength in KPa and/or mmHg (millimeters of mercury). Pincer muscle endurance would then be assessed by requiring the patient to pinch 50 percent of his/her maximum compression value in KPa and/or mmHg (millimeters of mercury) for an extended duration in seconds. The mandibular/pincer strain gauge can now be used as a therapy or exercise tool, if indicated (e.g. dysarthria involving the muscles of the mandible as they relate to mastication of food).

Figure 5:
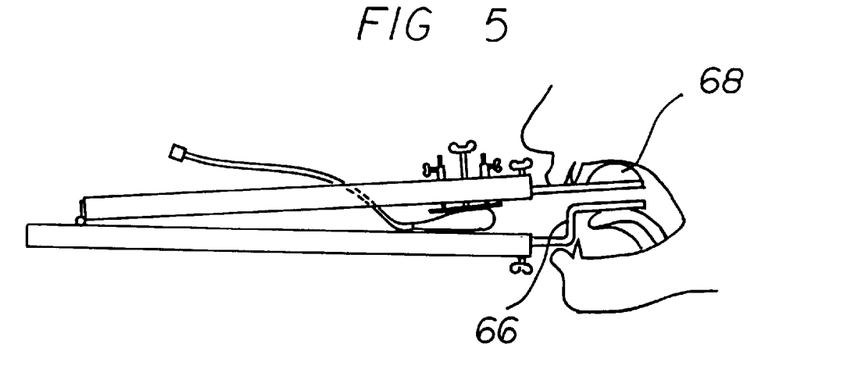
FIG. 5 is a side elevational view similar to FIG. 1, but illustrating a second embodiment of the invention for lingual elevation.
Figure 5B:
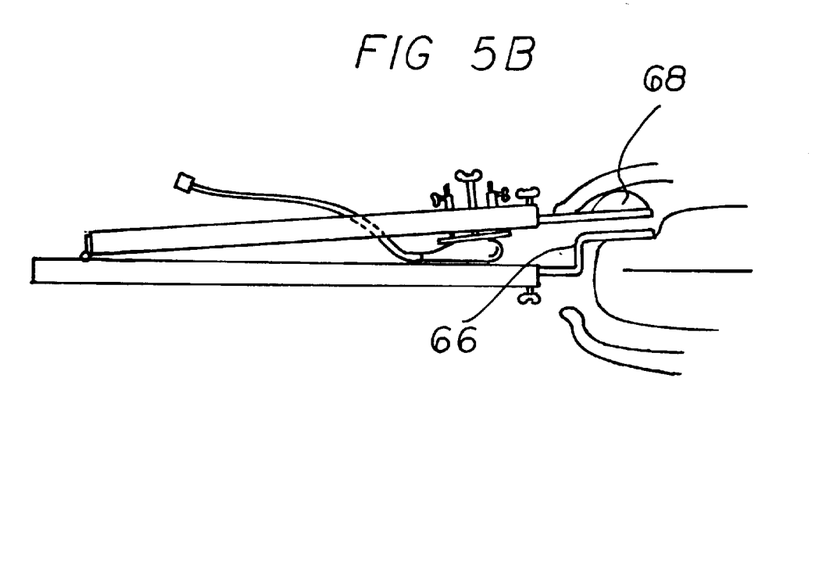
FIG. 5B is a side elevational view similar to FIG. 5, but illustrating the device positioned for lingual lateralization.
Figure 6:
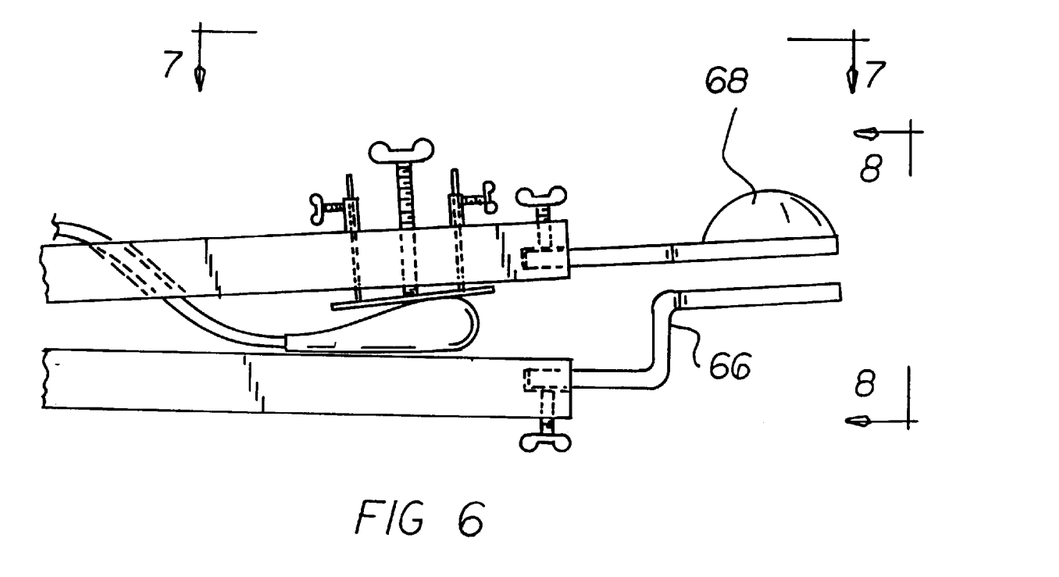
FIG. 6 is an enlarged side elevational view of the proximal portions of the device shown in FIG. 5.
Figure 7:
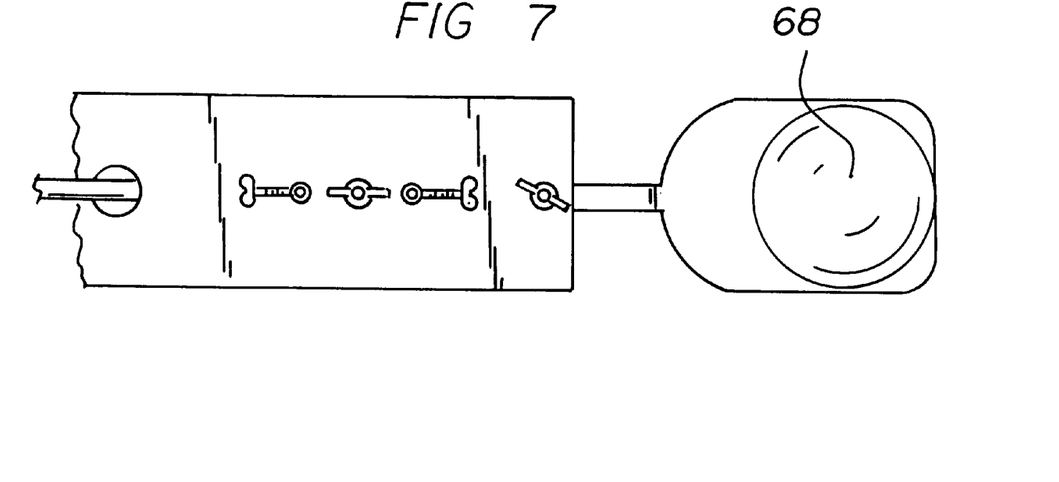
FIG. 7 is an end elevational view taken along line 7—7 of FIG. 6.
Figure 8:
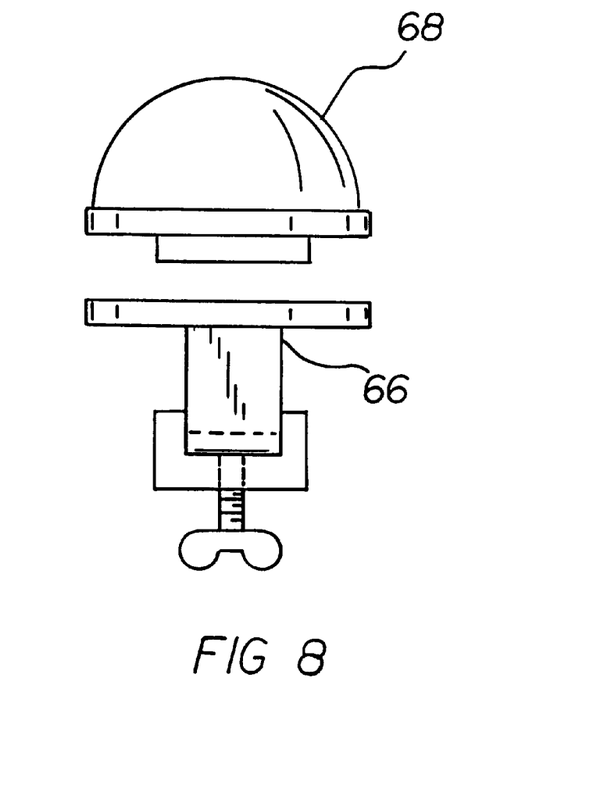
FIG. 8 is an end elevational view taken along line 8—8 of FIG. 6.
Figure 9:
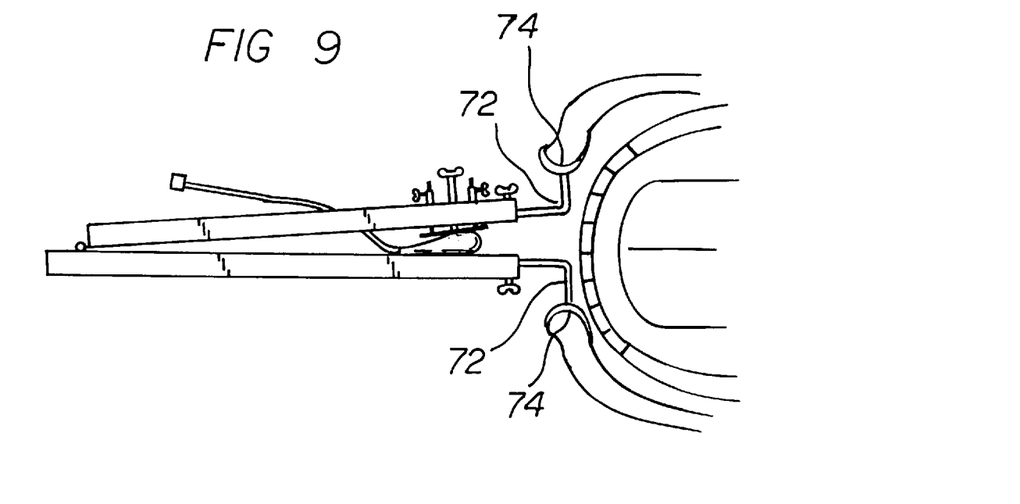
FIG. 9 is a side elevational view similar to FIG. 1 but illustrating a third embodiment of the invention.
Figure 10:
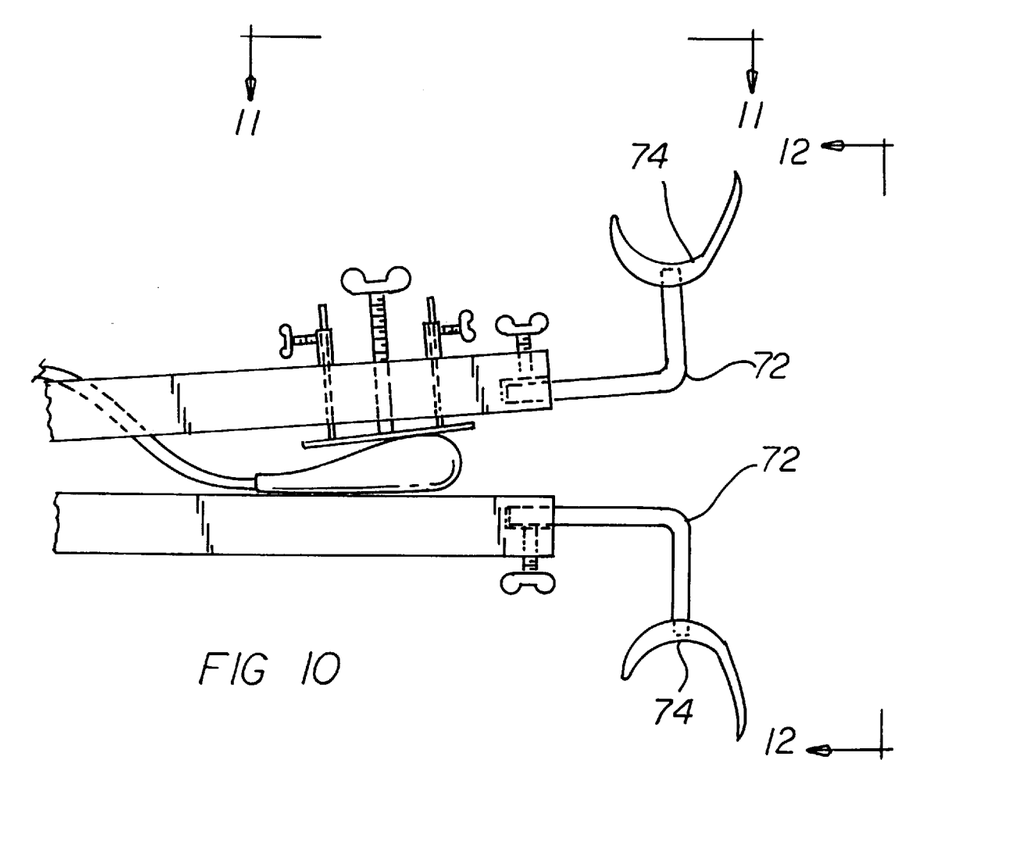
FIG. 10 is an enlarged side elevational view of the proximal end of the device shown in FIG. 9.
Figure 11:
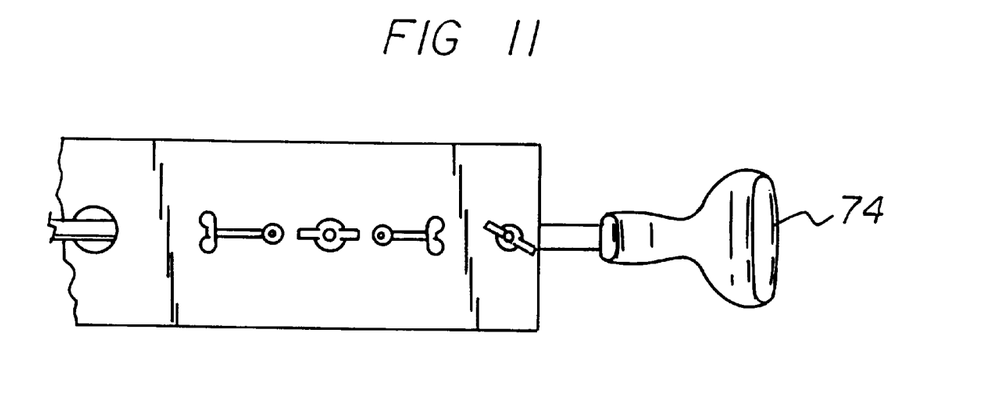
FIG. 11 is a top elevational view taken along line 11—11 of FIG. 10.
Figure 12:
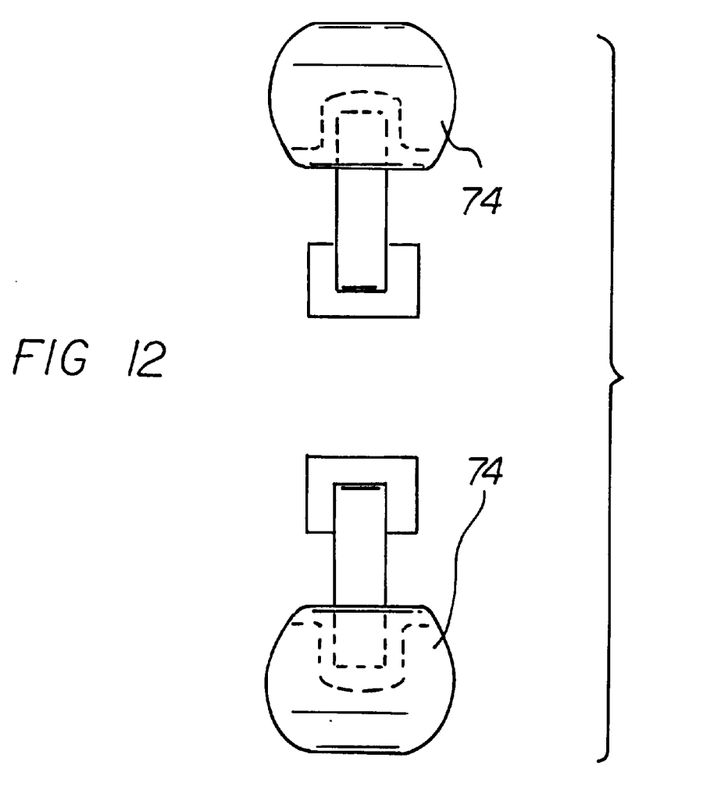
FIG. 12 is an end elevational view taken along line 12—12 of FIG. 10.
Figure 13:
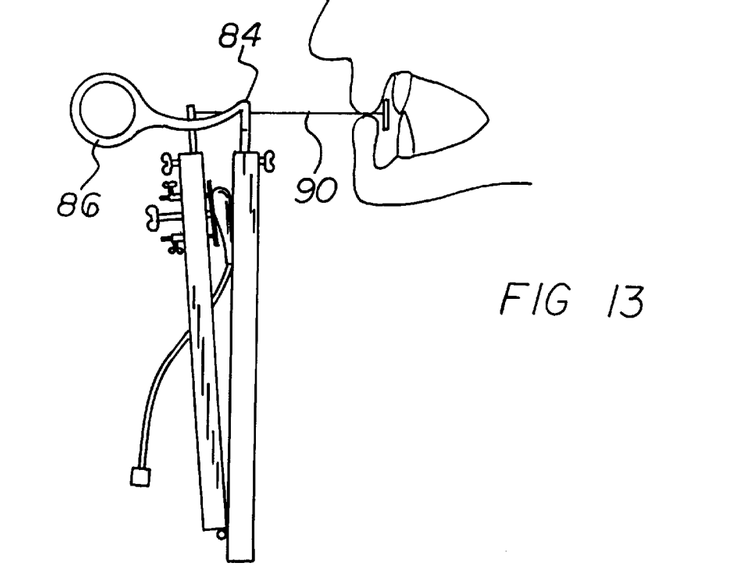
FIG. 13 is a side elevational view of a fourth alternate embodiment of the invention.
Figure 14:
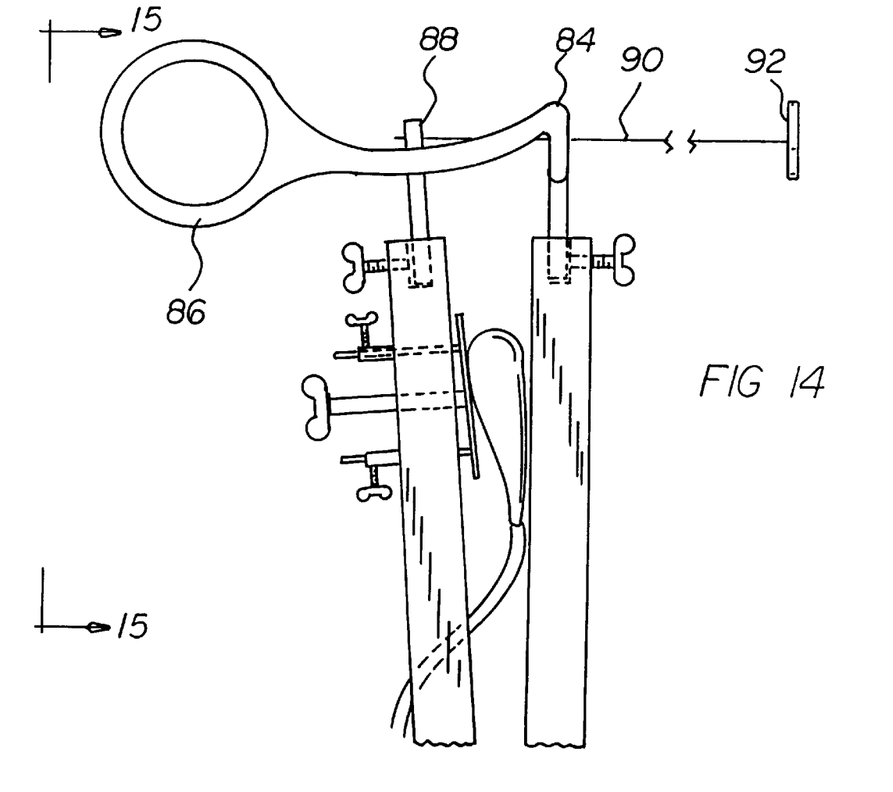
FIG. 14 is an enlarged side elevational view of the proximal end of the device shown in FIG. 13.
Figure 15:
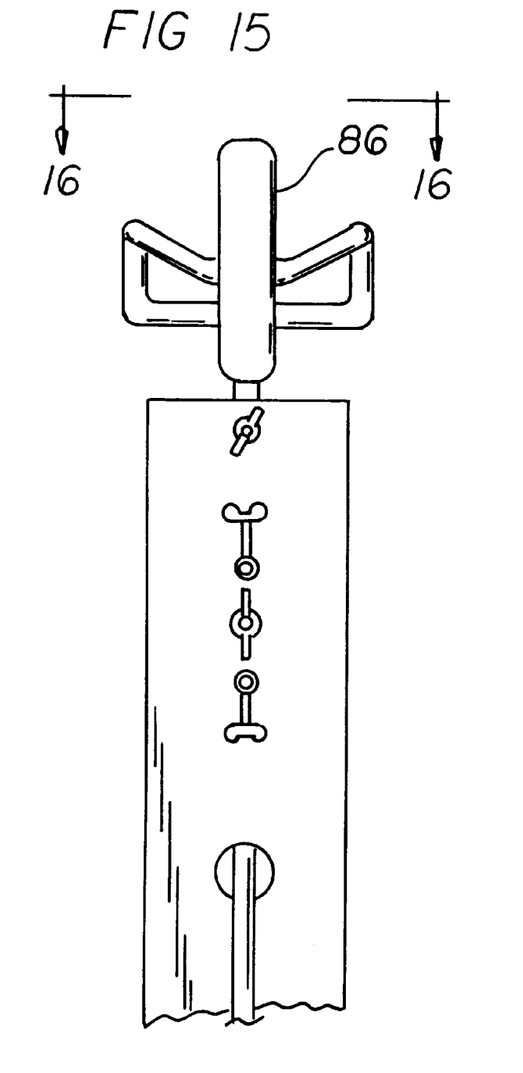
FIG. 15 is a top elevational view taken along line 15—15 of FIG. 14.
Figure 16:
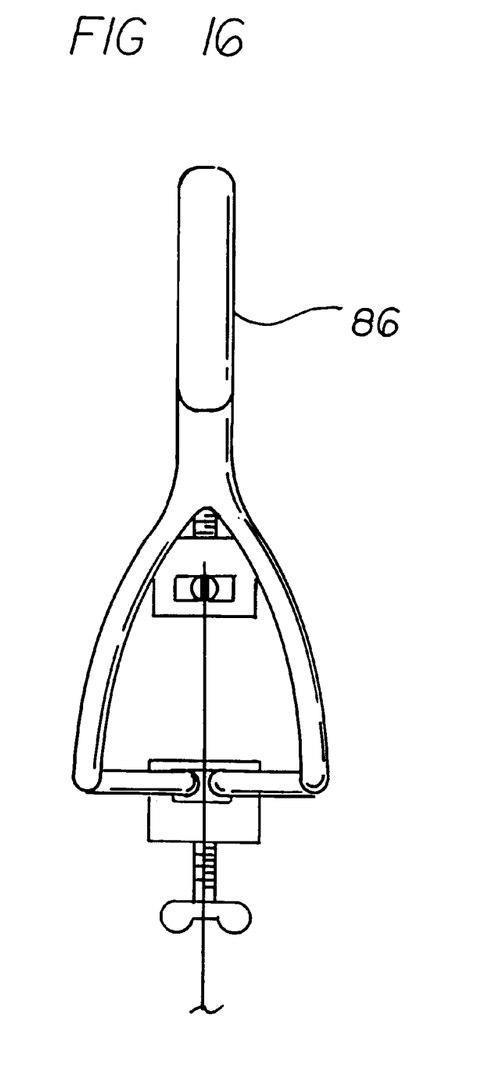
FIG. 16 is an end elevational view of the device shown in FIG. 14.

A second embodiment is shown in FIGS. 5–8 in which the lower support has a z-shaped profile 66 and the upper support has a pseudopalate or hemispherical projection 68 adapted to be contacted between a user's palate and tongue. This embodiment relates to a lingual strain gauge. The lingual strain gauge (LiSG) is the basic OD device with the attachment providing a pseudopalate and a tongue plate or lower support. This attachment allows the clinician to objectively assess lingual (tongue) strength and lingual endurance for lingual elevation, see FIG. 5, as well as for lingual lateralization towards the left and right buccal (inside of cheek) areas, see FIG. 5B. To assess the lingual elevation, the LiSG would be placed in the patient's mouth with the pseudopalate placed up against the roof of the patient's mouth and the tongue plate on top of the patient's tongue. The patient would then be required to push his/her tongue to the roof of his/her mouth as hard as he/she could. This in turn would compress the bulb in the OD. The pressure displacement would be sent through a catheter/plastic tubing from the bulb to a manometer. The manometer would then be read at it's peak pressure to determine the patient's maximum strength with this task. Next, the LiSG would be replaced in the same position in the patient's mouth and the patient would be required to elevate his/her tongue to the point of resisting 50 percent of his/her maximum strength in KPa and/or mmHg (millimeters of mercury) for an extended duration in seconds. This task would end when the patient was no longer able to resist 50 percent or more of his/her maximum strength in KPa and/or mmHg (millimeters of mercury). This task would be in the objective measurement of muscle endurance in the parameter of lingual elevation. To better illustrate this, if the patient compressed a maximum of 42 KPa while elevating his/her tongue as forcefully against the pseudopalate at the roof of his/her mouth during the strength assessment, then the muscle endurance would be determined objectively by determining how many seconds the patient could continue to resist greater than or equal to 50 percent of 42 KPa (which would be 21 KPa). The LiSG could then be rotated 90 degrees to the left or right to objectively assess lingual muscle strength and lingual muscle endurance in the context of lingual lateralization to the left and to the right buccal areas. For example, if the clinician rotated the LiSG 90 degrees to his/her left, then it would place the pseudopalate against the inside of the patient's right cheek and it would place the tongue plate or lower support against the right side of the patient's tongue. The distance between the pseudopalate and the tongue plate might then have to be readjusted using the adjustable plate guideshaft. The patient would now be required by the clinician to push his/her tongue against the tongue plate towards the right cheek as hard as he/she can. Both the muscle strength and the muscle endurance of the tongue in the contexts of right and left lateralization would be computed in the same way as with the abovementioned lingual elevation task. The lingual strain gauge can now be used as a therapy or exercise tool, if indicated (e.g. dysarthria involving the muscles of the tongue). The FIG. 5B illustration shows the embodiment of the second embodiment in an alternate location within a user's mouth.

A third embodiment is shown in FIGS. 9–12 in which the upper and lower support have a right-angle bend 72 with generally cylindrical surfaces 74 for receiving a user's lips. This relates to a labial protrusion gauge (LPG). The LPG is the basic OD device with the attachment providing two labial saddles (one for each corner of the mouth). The saddles would be placed into the corner of the patient's mouth and then muscle strength and muscle endurance could be objectively assessed by the clinician. Note FIG. 9. Muscle strength would be assessed by requiring the patient to protrude (pucker) his/her lips which would push the two saddles towards each other, compressing the bulb in the OD. The pressure displacement would be sent through a catheter/plastic tubing from the bulb to a manometer. The manometer would then be read at it's peak pressure to determine the patient's maximum strength with the task. Next, the LPG would be replaced between the corners of the patient's mouth, and the patient would be required to protrude his/her lips to the point of resisting 50 percent of his/her maximum strength in KPa and/or mmHg (millimeters of mercury) for an extended duration in seconds. This task would end when the patient was no longer able to resist 50 percent or more of his/her maximum strength in KPa and/or mmHg (millimeters of mercury). This task would be objective measurement of muscle endurance in the parameter of labial protrusion. To better illustrate this, if the patient compressed a maximum of 30 KPa while protruding his/her lips as forcefully against the labial saddles as possible during the strength assessment, then the muscle endurance would be determined objectively by determining how many seconds the patient could continue to resist greater than or equal to 50 percent of 30 KPa (which would be 15 KPa). The labial protrusion gauge can now be used as a therapy or exercise tool, if indicated (e.g. dysarthria involving the lips and adjoining muscles).

A fourth embodiment is shown in FIGS. 13–16 in which one of the supports has an L-shaped profile 84 with a ring 86 for being held by a user and the other support has a plate 88 with a string 90 and a button 92 adapted to be received within the lips of a user. This relates to a labial strain gauge (LaSG). The LaSG is the basic OD device with a button on a string attached to a handle. The button would be placed just behind the patient's lips, but in front of the central and lateral incisors. The clinician would then pull on the handle and determine muscle strength by seeing how many KPa and/or mmHg (millimeters of mercury) the patient could resist before his/her lips lose hold of the button. As the clinician pulls on the handle and the patient resists by keeping the button behind his/her lips, the two planks of the OD would compress the bulb inside. The pressure displacement would be sent through a catheter/plastic tubing from the bulb to a manometer. The manometer would then be read at it's peak pressure to determine the patient's maximum strength with the task. Next, the button would be replaced behind the patient's lips and the patient would be required to resist 50 percent of his/her maximum strain resistance in KPa and/or mmHg (millimeters of mercury) for an extended duration in seconds. This task would also typically end when the patient lost his/her labial hold on the button. This would be an objective measurement of muscle endurance. To better illustrate this, if the patient resisted 14 KPa before losing his/her labial hold on the button during the strength assessment of the orbicularis oris, then the muscle endurance of the orbicularis oris would be assessed by determining how many seconds the patient could continue to resist greater than or equal to 50 percent of 14 KPa (which would be 7 KPa) before losing hold of the labial button. The LaSG can now be used as a therapy or exercise tool, if indicated (e.g. dysarthria involving the lips and adjoining muscles).

Figure 17:
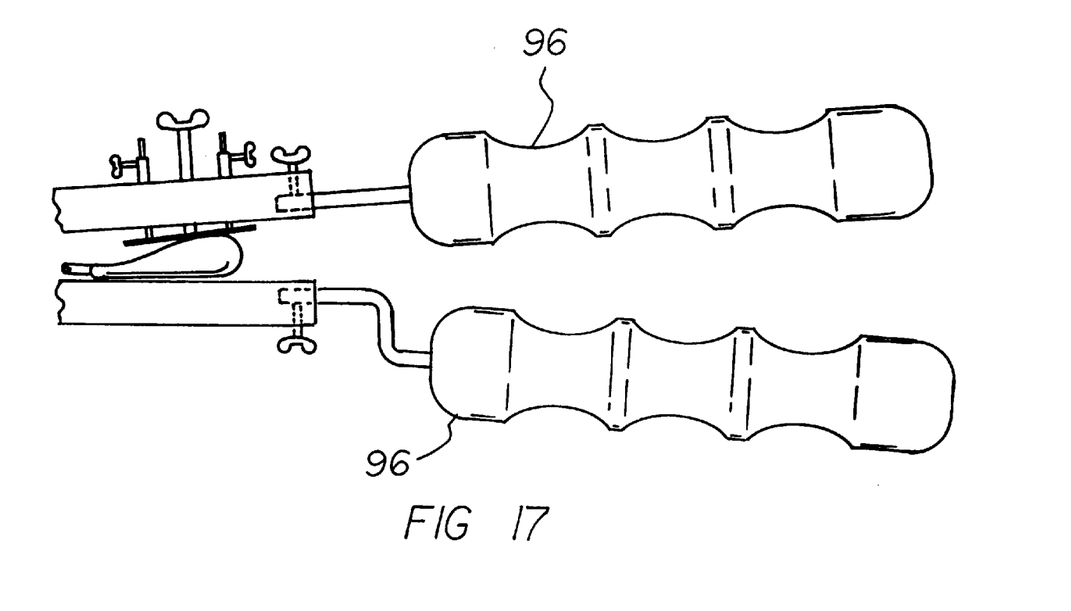
FIG. 17 is a side elevational view of an embodiment similar to the embodiment of FIG. 1 but constructed for hand use.

The final embodiment is shown in FIG. 17. Such embodiment is similar to the primary embodiment of FIGS. 1–4 except that supports 26, 28 are removed and replaced by handles 96. the handles are adapted to be grasped by the hands of a user to determine the strength of the user's grip.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved system for measuring a plurality of characteristics of a user's oral regions comprising, in combination:

a pair of planks each having a proximal end and a distal end, the planks including an upper plank and a lower plank, the lower plank being of a length greater than the upper plank with a hinge coupling the distal ends of the planks, an axial recess formed in the proximal end of each plank with a threaded aperture operatively associated with each recess;

a pair of proximally extending supports each having an exterior surface adapted to be received in the mouth of a user and to be moved toward each other upon the application of the user's teeth toward each other, the supports each having a distal end received within an associated recess adjacent to the proximal end of the upper plank and the proximal end of the lower plank respectively with an associated wing nut for securing the supports to the planks and for allowing the separation therebetween;

a deformable pneumatic bulb positioned between the planks adjacent to the proximal end thereof with an associated tube having a first end coupled to the bulb and adapted to be compressed upon the application of force by a user to the supports through the planks to thereby apply a pneumatic force to the second end of the tube;

a meter coupled to the second end of the tube to provide readings in response to the force applied to the bulb, the tube extending through a hole in the upper plank and;

an adjustment plate adjustably secured to the lower surface of the upper plank with a threaded wing nut adapted to allow the selective positioning of the adjustment plate with respect to the upper plank as a function of the pressure intended to be applied by the user, the adjustment plate including two parallel guide rods extending upwardly therefrom through parallel apertures in the upper plank with securement sleeves with apertures and small wing nuts to assist in the proper positioning of the adjustment plate.

2. A system for measuring a plurality of characteristics of a user's oral regions comprising, in combination:

a pair of planks each having a proximal end and a distal end, the planks including an upper plank and a lower plank with a hinge coupling the distal ends of the rods;

a pair of proximally extending supports each having an exterior surface adapted to be received in the mouth of a user;

a deformable pneumatic bulb positioned between the planks adjacent to the proximal end thereof with an associated tube to thereby apply a pneumatic force to the second end of the tube and;

a meter coupled to the second end of the tube to provide readings in response to the force applied to the bulb, the tube extending through a hole in the upper rod.

3. The system as set forth in claim 2 wherein an adjustment plate is adjustably secured to the lower surface of the upper plank with a threaded wing nut adapted to allow the selective positioning of the adjustment plate with respect to the upper plank as a function of the pressure intended to be applied by the user, the adjustment plate including two parallel guide rods extending upwardly therefrom through parallel apertures in the upper plank with securement sleeves with apertures and small wing nuts to assist in the proper positioning of the adjustment plate.

4. The system as set forth in claim 2 wherein the lower support has a generally z-shaped profile to allow pressure to be applied by a user's teeth.

5. The system as set forth in claim 2 wherein the lower support has a z-shaped profile and the upper support has a hemispherical projection adapted to be contacted between a user's palate and tongue.

6. The system as set forth in claim 2 wherein the upper and lower supports have a right-angle bend with generally cylindrical surfaces for receiving a user's lips.

7. The system as set forth in claim 2 wherein one of the supports has an L-shaped profile with a ring for being held by a user and the other support has a plate with a string and a button adapted to be received within the lips of a user.

8. The system as set forth in claim 2 and further including a pair of handles couplable to the pair of planks.

* * * * *